(12) United States Patent
Coe et al.

(10) Patent No.: US 6,623,671 B2
(45) Date of Patent: Sep. 23, 2003

(54) LIPOSOME EXTRUSION PROCESS

(76) Inventors: Royden M. Coe, 17 Hanover Ct., Bordentown, NJ (US) 08505; Robert L. Thies, 2241 Dunbar St., Vancouver, British Columbia (CA), V6R 3M8; Joel B. Portnoff, 76 Gregory Pl., Richboro, PA (US) 18954

( * ) Notice: Subject to any disclaimer, the term of this patent is extended or adjusted under 35 U.S.C. 154(b) by 0 days.

(21) Appl. No.: 09/988,665

(22) Filed: Nov. 20, 2001

(65) Prior Publication Data

US 2002/0050660 A1 May 2, 2002

Related U.S. Application Data

(63) Continuation of application No. 08/441,569, filed on May 15, 1995, now abandoned, which is a continuation of application No. 08/203,638, filed on Mar. 1, 1994, now abandoned, which is a continuation of application No. 07/771,267, filed on Oct. 4, 1991, now abandoned, which is a continuation-in-part of application No. 07/593,200, filed on Oct. 5, 1990, now abandoned.

(51) Int. Cl.$^7$ .................... B01J 13/20; A61K 9/127; A61K 9/133
(52) U.S. Cl. ................. 264/4.3; 424/450; 428/402.2
(58) Field of Search .............. 264/4.1, 4.3; 428/402.2; 424/450

(56) References Cited

U.S. PATENT DOCUMENTS

| | | | |
|---|---|---|---|
| 4,522,803 A | 6/1985 | Lenk et al. | 424/1.1 |
| 4,529,561 A | 7/1985 | Hunt et al. | 264/4.3 |
| 4,588,578 A | 5/1986 | Fountain et al. | 424/1.1 |
| 4,687,551 A | 8/1987 | Furneaux et al. | 204/11 |
| 4,737,323 A | 4/1988 | Martin et al. | 264/4.3 |
| 4,752,425 A | 6/1988 | Martin et al. | 264/4.6 |
| 4,766,046 A | 8/1988 | Abra et al. | 424/450 |
| 4,927,637 A | 5/1990 | Morano et al. | 424/450 |
| 5,008,050 A | 4/1991 | Cullis et al. | 264/4.3 |
| 6,217,899 B1 * | 4/2001 | Benameur et al. | 424/450 |

FOREIGN PATENT DOCUMENTS

| | | |
|---|---|---|
| WO | 86/00238 | 1/1986 |
| WO | 88/07850 | 10/1988 |
| WO | 91/10422 | 7/1991 |

OTHER PUBLICATIONS

Anotec Separations, Manufacturer's Literature, "Anotec Inorganic Membrane Filtration", New York (1988).
Anotec Separations, Manufacturer's Literature, "Anotec Separation Catalogue", New York (Feb. 1989).
Anotec Separations, Manufacturer's Literature, "Anotec Porous Tissue Culture Plate Insert", New York (Sep. 1989).
Bangham et al., "Diffusion of Univalent Ions Across the Lamellae of Swollen Phospholipids", *J. Mol. Bio.*, 13:238–252 (1965).
Deamer et al., "Liposome Preparations: Methods and Mechanisms", in *Liposomes*, edited by M. Ostro, Marcel Dekker, Inc., New York, pp. 27–51 (1983).
Deamer et al., "Large Volume Liposomes by an Ether Vaporization Method", *Biochemica et Physica Acta*, 443:629–34 (1976).
Fifield, "Sterilization Filtration", in *Disinfection, Sterilization, and Preservation*, 2$^{nd}$ Edition, edited by S. Block, Lea & Febiger, Philadelphia, pp. 562–591 (1977).
Furneaux et al., "The Formation of Controlled–Porosity Membranes from Anodiacally Oxidized Aluminium", *Nature*, 337:147–9 (1989).
Hoffman, "Inorganic Membrane Technology in Sample Preparation", *American Laboratory News Edition*, Apr. 1989.
Jones et al., "Comparison of a new Inorganic Membrane Filter (Anopore) with a Track–Etched Polycarbonate Membrane Filter (Nuclepore) for Direct Counting of Bacteria", *Applied and Environmental Microbiology*, 55(2):529–30 (1989).
Papahadjapoulos et al., "Phospholipid Model Membranes I. Structural Characteristics of Hydrated Liquid Crystals", *Biochemica Biophysica Acta*, 135:624–638 (1967).
Szoka et al., "Procedure for preparation of Liposomes with large internal aqueous space and high capture by reverse–phase evaporation," *Proc. Natl. Acad. Sci.*, USA, 75(9):4194–8 (1978).
Schullery et al., "Studiess on Phosphatidylcholine Model Membranes–Size–Heterogencity Effect on Permeability Measurements", *Chem. Rhys. Lipids*, 12:75–95 (1973).
Szoka et al., "Comparative Properties and Methods of Preparation of Lipid Vesicles (Liposomes)", *Ann. Rev. Biophys. Bioeng.*, 9:567–508 (1980).

* cited by examiner

Primary Examiner—Richard D. Lovering
(74) Attorney, Agent, or Firm—Burns, Doane, Swecker & Mathis, LLP

(57) ABSTRACT

A method of sizing liposomes by passing a suspension of liposomes through an aluminum oxide porous film by entering the film via the smaller pores and extruded via the larger pores, under pressure, is disclosed. In a preferred embodiment, the porous film is a branched-pore type anodic aluminum oxide porous film. The process produces a population of liposomes substantially free of liposomes above a predetermined maximum size. Also disclosed is an apparatus for carrying out the invention.

12 Claims, 2 Drawing Sheets

LIPOSOME EXTRUSION PROCESS

CROSS-REFERENCES TO RELATED APPLICATIONS

This is a continuation of U.S. application Ser. No. 08/441,569, filed May 15, 1995, now abandoned, which is a continuation of U.S. application Ser. No. 08/203,638, filed Mar. 1, 1994, now abandoned, which is a continuation of U.S. application Ser. No. 07/771,267, filed Oct. 4, 1991, now abandoned, which is a continuation-in-part of U.S. application Ser. No. 07/593,200, filed Oct. 5, 1990, now abandoned.

FIELD OF THE INVENTION

This invention relates to a method of sizing liposomes, and more particularly to a sizing method which includes extruding liposomes through a branched-pore type aluminum oxide porous film.

BACKGROUND OF THE INVENTION

Liposomes are completely closed lipid bilayer membranes containing an entrapped aqueous volume. Liposomes may be unilamellar vesicles (possessing a single bilayer membrane) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

The original liposome preparation of Bangham, et al. (J. Mol. Biol., 1965, 13:238–252) involves suspending phospholipids in an organic solvent which is then evaporated to dryness leaving a phospholipid film on the reaction vessel. Next, an appropriate amount of aqueous phase is added, the mixture is allowed to "swell", and the resulting liposomes, which consist of multilamellar vesicles (MLVs), are dispersed by mechanical means. This technique provided the basis for the development of the small sonicated unilamellar vesicles (SUVS) described by Papahadjopoulos et al. (Biochim. Biophys. Acta., 1968, 135:624–638), as well as large unilamellar vesicles (LUVs). In addition, U.S. Pat. No. 4,235,871, issued Nov. 25, 1980 to Papahadjopoulos et al., describes a "reverse-phase evaporation process" for making oligolamellar lipid vesicles, also known as reverse-phase evaporation vesicles (REVs).

Alternative methods have been developed for forming improved classes of multilamellar vesicles which have been shown to have particularly improved properties such as, for example, higher active ingredient trapping efficiencies and loadability, better stability, less leakage, and greater ease of production. One such improved class of liposomes, denominated as stable plurilamellar vesicles (SPLVs), is described in U.S. Pat. No. 4,522,803, issued Jun. 11, 1985 to Lenk et al. Another such improved class, defined as monophasic vesicles (MPVs), is described in U.S. Pat. No. 4,558,578, issued May 13, 1986 to Fountain et al. Both of these classes of liposomes have also been characterized as having substantially equal interlamellar solute distributions. A general review of various methods for producing liposomes, including an extensive bibliography, is set forth in Deamer and Uster, "Liposome Preparation: Methods and Mechanisms", in the Liposomes, edited by M. Ostro, pp. 27–51 (1983), incorporated herein by reference.

The administration of drugs encapsulated in or otherwise associated with liposomes has been proposed for use in a variety of drug delivery regimens in combination with or as an alternative to the administration of free drugs. In some applications, liposomes have been found to provide sustained release of drugs for extended periods, which can be of particular importance in the lengthy chemotherapy regimens often required for the treatment of various forms of cancer or AIDS-related illnesses. Another property of liposomes is their ability to be taken up by certain cells, such as phagocytes, such that they can deliver their active ingredient to the interior of the cells. This makes such liposome treatment particularly useful in treating intracellular infections, such as those associated with species of Mycobacteria, Brucella, Listeria, and Salmonella. Thus, drugs encapsulated in liposomes can be delivered for the treatment of such intracellular diseases without administering large amounts of free unencapsulated drug into the bloodstream. In addition, the mere association of certain drugs or other bio-active agents with liposomes has been found to potentiate or improve the activity of such drugs or bio-active agents, or to reduce their toxicity.

Liposomes behave like particles, and are commonly described in terms of average particle size and particle-size distributions. For certain uses of liposomes, particularly in the parenteral administration of drugs, it is important to size the liposomes to a desired average particle size, and to maintain a controlled particle-size distribution, particularly by sizing the liposomes so that substantially all of the liposomes are of a size below a predetermined maximum diameter. For liposomes intended for parenteral administration, one desirable size range is between about 100 and 1000 nm, preferably between about 100 and 500 nm. (As used herein, nm represents nanometer ($10^{-9}$ m) and um represents micrometer or micron ($10^{-6}$ m).) The maximum desired size range is often limited by the desire to sterilize the liposomes by filtering through conventional sterilization filters, which commonly have a particle-size discrimination of about 200 nm. However, overriding biological efficacy and/or safety factors may dictate the need for a particular particle size, either larger or smaller. Control of the size range of the liposomes may also improve the effectiveness of the liposomes in vivo, as well as the stability and leakage resistance of the liposomes.

The various methods for producing liposomes generally produce a suspension of liposomes of widely varying sizes, many of which exceed 1000 nm in average particle size. A number of methods have been proposed to reduce the size and size distribution of liposomes in such suspensions. In a simple homogenization method, a suspension of liposomes is repeatedly pumped under high pressure through a small orifice or reaction chamber until a desired average size of liposome particles is achieved. A limitation of this method is that the liposome size distribution is typically quite broad and variable, depending on the number of homogenization cycles, pressures, and internal temperature.

Small unilamellar vesicles (SUVs), generally characterized as having diameters below 100 nm, are composed of highly strained, curved bilayers. The SUVs are typically produced by disrupting larger liposomes via ultrasonication. It has been found that a narrow size distribution of such liposomes can only be achieved when the liposomes have been reduced to their smallest sizes, less than about 50 nm. Furthermore, this process may not be amenable to large-scale production, because it is generally conducted as a batch process with long-term sonication of relatively small volumes. In addition, heat build-up during sonication can lead to peroxidative damage to lipids, and sonication probes may shed titanium particles which are potentially quite toxic in vivo.

A method of sizing liposomes by filtration through a 200-nm Unipore™ polycarbonate filter is discussed in Szoka, *Proc. Natl. Acad. Sci. U.S.A.*, 75:4194–8 (1978). A size-processing method based on liposome extrusion through a series of uniform straight-pore type polycarbonate membranes from about 1000 nm down to about 100 nm is described in Hunt et al., U.S. Pat. No. 4,529,561, issued Jul. 16, 1985. However, this method can be relatively slow, often requiring many passes through various size filters to obtain the desired particle-size distribution.

Vesicles may also be size-reduced using an extrusion process described in Cullis et al., U.S. Pat. No. 5,008,050, issued Apr. 16, 1991, incorporated herein by reference. Vesicles made by this technique are extruded under pressure through a filter with a pore size of 100 nm or less. This procedure avoids the problems of the above homogenization and sonication methods, and does not require multiple passes through decreasing size filters, as described in the above-cited U.S. Pat. No. 4,529,561. Such a process can provide size distributions of liposomes that are quite narrow, particularly by cycling the material through the selected size filter several times. In addition, it is believed that such extrusions may convert multilamellar vesicles into oligolamellar or even unilamellar form, which may be desired for certain applications. However, as demonstrated by the Examples set forth below in the present specification, when such extrusions are made through 100-nm polycarbonate filters, such as the Nuclepore™ filters used in the examples of this reference, even at relatively high pressures flow rates may be relatively low.

U.S. Pat. No. 4,737,323, issued Apr. 12, 1988, describes a method for sizing liposomes by extrusion through an asymmetric ceramic filter. Such filters are designed for operation at relatively high pressure, and can be backflushed to prevent clogging. U.S. Pat. No. 4,927,637, issued May 23, 1990 describes a method of sizing liposomes by passing them through a polymer filter having a web-like "tortuous-path" construction.

An alternative type of filter medium is described in Furneaux et al., U.S. Pat. No. 4,687,551, issued Aug. 18, 1987. This patent discloses a new type of filter sheet comprising an anodic aluminum oxide film having branched pores extending from one surface of the film to the other. The film is unique in that it includes a system of larger pores extending in from one face and a system of smaller pores extending in from the other face. The system of larger pores interconnects with the system of smaller pores such that the inner ends of one or more smaller pores are joined to the inner end of a larger pore and there are substantially no blind larger pores. This patent is incorporated by reference into the present specification for the purpose of disclosing such branched-pore type aluminum oxide porous films and the method for forming them.

In a particular embodiment, the branched-pore anodic aluminum oxide film of the Furneaux et al. patent is described as:

An anodic aluminum oxide film having pores extending from one face of the film to the other,
including a system of larger pores extending in from one face a distance into the film, the larger pores having a diameter d near their inner ends, and a system of smaller pores extending in from the other face a distance s into the film, the smaller pores having a substantially uniform minimum diameter p,
the system of larger pores interconnecting with the system of smaller pores, such that the inner ends of one or more smaller pores are joined to the inner end of a larger pore and there are substantially no blind larger pores, wherein
d is 10 nm to 2 um
p is at least 2 nm but less than 0.5 d, and
s is 10 nm to 1 um.

The size rating of such branched-pore type films is equal to p, the substantially uniform minimum diameter of the smaller pores.

Filtration membranes made in accordance with the disclosure of the Furneaux et al. patent are commercially available and sold by the Anotec Separations, New York, N.Y., under the name Anopore™. Additional information regarding such branched-pore type membranes is provided in Furneaux et al., "The Formation of Controlled-Porosity Membranes from Anodicaily Oxidized Aluminum", *Nature* 337:147–9 (1989).

One use of such branched-pore Anopore™ filters is described in Jones et al., "Comparison of a New Inorganic Membrane Filter (Anopore) with a Track-Etched Polycarbonate Membrane Filter (Nuclepore) for Direct Counting of Bacteria", *Applied and Environmental Microbiology* 55(2):529–30 (1989). This article compares the bacteria filtering ability of a 200-nm-pore-size Anopore™ filter against a 200-nm-pore-size Nuclepore™ filter.

SUMMARY OF THE INVENTION

In accordance with the method of the present invention, a population of liposomes substantially free of liposomes above a predetermined maximum size is produced by (1) providing a suspension of liposomes, a portion of which are of sizes larger than the predetermined maximum size; and (2) passing the suspension under pressure one or more times through an aluminum oxide porous film.

Films with a pore size of 1000 nm or less may be used to obtain liposomes with an average particle size of in the range of about 100 to 1000 nm. In a particular embodiment of the present invention, a film with a pore-size rating of 200 nm or less is used to obtain a population of liposomes with a predetermined maximum diameter of less than about 500 nm. In another embodiment, a film with a Pore size of about 100 nm or less is used, and the suspension of liposomes is passed through the filter one or more times until the average liposome particle size is about 100 to 200 nm.

In a further embodiment of the present invention, the suspension of liposomes is passed repeatedly through the porous film until a desired particle size distribution is obtained. In a particular embodiment, the liposomes are passed through the porous film two to ten times. In an additional embodiment, the liposomes are presized by being passed one or more times through a 2–10 micrometer filter.

A preferred film for use in the present invention is a branched-pore type anodic aluminum oxide porous film. As discussed above, such a branched-pore anodic aluminum oxide porous film is an aluminum oxide sheet having two substantially parallel major faces with pores extending from one face of the sheet to the other, including a system of larger pores extending from one face into the sheet and a system of smaller pores extending in from the other face, the system of larger pores interconnecting with the system of smaller pores such that the inner ends of one or more smaller pores are joined to the inner end of a larger pore and there are substantially no blind larger pores. The size rating of such branched-pore type films is equal to the minimum diameter of the smaller pores, which are preferably substantially uniform.

In a further embodiment of the present invention, apparatus is provided for carrying out the filtration method. The apparatus comprises one or more filter assemblies for holding the aluminum oxide porous films in operational configuration, means for supplying the suspension of liposomes to the filter assemblies, and means to receive the filtrate from the assemblies. In a particular embodiment, two or more assemblies are used in parallel configuration to filter the liposome suspension passing from the supply means to the receiving means. Optionally, means can also be provided for recirculating at least a portion of the filtrate from the receiving means back to the supply means, thus providing for multiple passes of the liposomes through the filters. In addition, a sterilization filter can be provided downstream of the receiving means, as may be appropriate to prepare the filtrate for pharmaceutical use.

The extrusion is rapid and inexpensive, and does not require the use of solvents or other chemicals that must be removed.

DETAILED DESCRIPTION OF THE INVENTION

Figure 1:
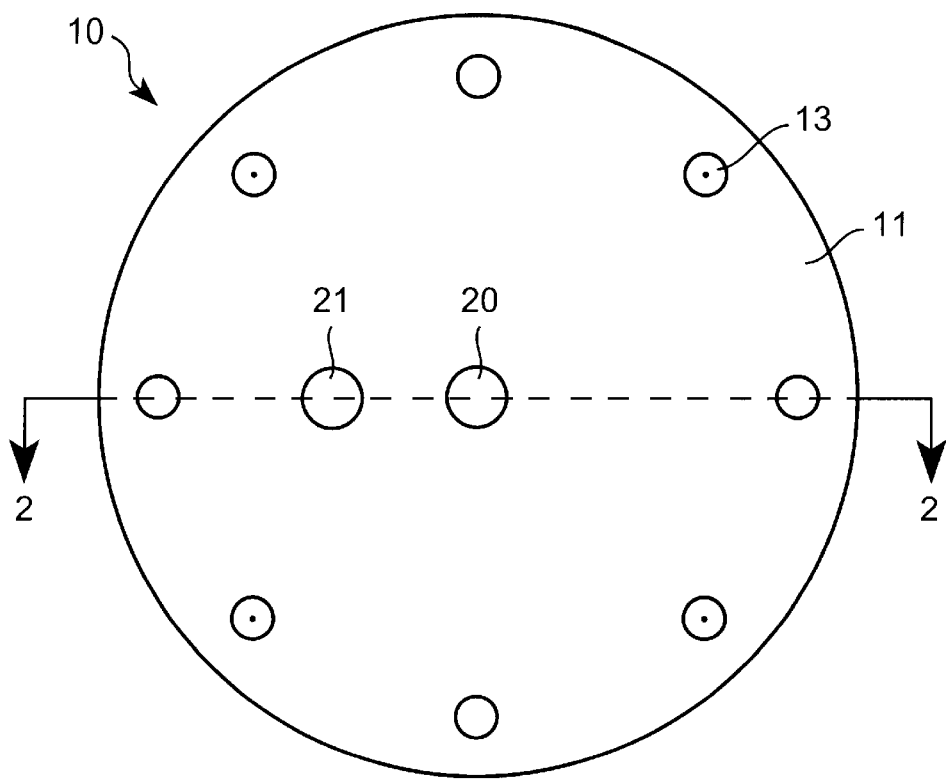
FIG. 1 is a simplified top view, not to scale, of a filter assembly made in accordance with the present invention.

As discussed in the Furneaux et al. references cited above, aluminum can be anodized in acid to produce a uniform array of cells or openings having cylindrical pores which preferably branch from larger pore-size openings in one face of the film to smaller pore-size openings in the other face of the film. Such filters are available in a variety of pore sizes, and ones having a pore size of the smaller pores of less than about 1000 nm are preferred for use in the present invention, although smaller or larger pore-sizes can be used depending on the final application of the liposomes. (Hereinafter, unless otherwise noted, "pore size" for such filters shall refer to the minimum pore size of the smaller pores.) At present, of the Anopore™ anodized aluminum porous filters commercially available from Anotec Separations, those of pore size under 200 nm are of the branched-pore structure, and those of pore size of 200 nm or larger are of uniform pore size from one surface to the other. When the desired average particle size of the liposomes is less than about 200 nm, then the preferred pore size of the filter is less than about 100 nm. These filters are also of the preferred branched-pore type structure.

These aluminum oxide filters are hydrophilic; they do not swell in aqueous solvents; they have good organic solvent resistance; and they have pores of uniform size which promote high flow-through characteristics. Because of the properties of such films, it was found that liposomes could be extruded through them at relatively high flow rates under relatively low pressure (see Example 3, below). Thus, aluminum oxide filters are shown to be superior for extruding liposomes over the previously known polymeric filters.

In the present invention, the branched-pore filters are preferably used so that the liposomes enter the face with the smaller size pores and exit though the face with the larger size pores. However, as shown in the examples below, good extrusion can also be obtained with a filter mounted in the inverted position, so that the liposomes enter the large pore-size face.

In accordance with the process of present invention, a population of liposomes substantially free of liposomes above a predetermined maximum size is produced from a suspension of liposomes, a portion of which are of sizes larger than the predetermined maximum size. The process includes passing the suspension of liposomes under pressure one or more times through an aluminum oxide porous film, such as one of the type described above.

To determine whether a population of liposomes is "substantially free of liposomes above a predetermined maximum size", the liposomes can be tested using a standard sizer. One such standard sizer is a Malvern Sizer, available from Malvern Instruments, Malvern, England, which is described and used in some of the examples below. Another sizer which can used to determine particle size distributions is a Nicomp™ laser particle sizer, available from Hiac/Royco Instruments, Menlo Park, Calif., which is also described and used in some of the examples below. In the particle size distributions reported in the examples below, a test result indicating that 0.0 percent of the liposomes present in the population are above a given size indicates that the population is "substantially free" of such large-size liposomes.

Although not required, the particle size, and particularly the particle-size distribution, of liposomes may be made smaller and more uniform by extruding though a larger filter as a first step. For example, extruding the liposomes through a suitable filter of 2–10 micrometer size, such as one made from polytetrafluoroethylene (PTFE), as is well known in the art, will reduce the particle size and particle-size distribution prior to extruding through the aluminum oxide filter, and may thereby reduce the time for extrusion.

The pressure during the extrusion will be varied depending upon the liposomes employed, their mean particle diameter and particle-size distribution, and the rate of flow desired. Extrusion pressures may vary from about 200 to about 1000 psi (1.4–6.9 MPa), but pressures of less than about 600 psi (4.2 MPa) are preferred.

In general, fewer extrusion passes are required when using the branched-pore type aluminum oxide filters of the present invention, as opposed to the previously known polycarbonate filters, for similar results in terms of particle size, particle-size distribution and flow rates. However, repeated extrusion passes through the aluminum oxide filters may be used to obtain a narrower particle-size distribution, and particularly to reduce all liposomes to below a predetermined maximum size. For example, 2–10 extrusions of the liposomes through the filters are preferred to decrease the particle-size distribution, thereby producing relatively uniform liposomes of high capacity in a rapid, efficient and inexpensive manner. Multiple extrusions may also convert multilamellar vesicles to more desired oligolamellar or unilamellar forms.

Subsequent to the extrusion process of the invention, any free unencapsulated therapeutic agent or other solution can be readily removed, as by dialysis or diafiltration, leaving stable drug encapsulating liposomes of relatively uniform size. The resultant liposomes may be readily measured into uniform dosages for administration parenterally or orally.

The invention will be further illustrated by the following examples, but the invention is not meant to be limited to the details described therein.

EXAMPLE 1

Preparation of Liposomes

Three batches of liposomes (hereinafter designated A, B and C) were prepared as follows:

71.3 mg/ml egg phosphatidylcholine (obtained from Princeton Lipids, Princeton, N.J.) and 28.7 mg/ml cholesterol (J. T. Baker, Phillipsburg, N.J.) were dissolved in 0.15 to 0.5 ml of methylene chloride and added to a 300-mM citrate buffer solution (pH 4.0) to make up a 1-ml volume. The methylene chloride was removed by heating the mixture to about 40° C. To aid in the removal of the solvent, nitrogen was sparged through Batches A and C, while Batch B was heated under partial vacuum.

The resultant liposomes were vesicles of various sizes and various size distributions. The initial size distributions of these liposomes prior to size reduction were measured on a Malvern Sizer 3600 E Type with a 63-mm lens, available from Malvern Instruments, Malvern, England. The results are presented in Table I, in which the mean diameters and size distribution ranges are expressed in micrometers (um). Before extrusion, Batch B was presized through a 5-um pore-size Mitex™ PTFE filter (Millipore Corp., Bedford, Mass.), and the mean diameter and distribution range for the Batch B liposomes after presizing is included in the table. Batches A and C were not put through presizing. The results show a considerable batch-to-batch variation in the size distribution of the unsized liposomes.

TABLE I

Liposome Sizes Prior to Extrusion

| Batch | Mean Diameter (um) | Distribution Range (um) |
|---|---|---|
| A | 23.2 | 1.5–118 |
| B | 14.9 | 1.5–118 |
| B* | 2.5 | <1.2–5 |
| C | 3.3 | <1.2–14 |

*After 5 micrometer presizing

EXAMPLE 2

Extrusion of Liposomes

In accordance with the present invention, the liposomes of Example 1 were extruded five times under pressure through an Anopore™ 90-mm diameter, 100-nm pore size (small pores) branched-pore aluminum oxide filter of the type described above. The placement of the filter for Batches A and B was with the input through the small-pore surface. Good results were also obtained for Batch C, which was extruded with the filter inverted so that the input was through the large-pore surface. The mean diameter of the liposomes and the particle-size distributions of the liposomes were measured after the indicated passes through the filter. The size distributions were measured on a Nicomp™ Model 370 laser particle sizer, available from Hiac/Royco Instruments, Menlo Park, Calif. The results measured after each extrusion pass are summarized in Table II:

TABLE II

Mean Diameter and Particle Size Distribution After Each Extrusion Pass

| Pressure PSI (MPa) | Extrusion Rate Liters/min | Mean Diameter (um) | <0.1 um percent | 0.1– 0.45 um percent | >0.45 um percent |
|---|---|---|---|---|---|
| Batch A: | | | | | |
| 325 (2.2) | NT | NT | NT | NT | NT |
| | 0.2 | 0.188 | 2.6 | 94.4 | 3.0 |
| | 0.2 | 0.168 | 6.7 | 92.6 | 0.8 |
| | 0.2 | 0.132 | 7.6 | 92.3 | 0.0 |
| | 0.2 | 0.123 | 3.6 | 96.4 | 0.0 |
| Batch B: | | | | | |
| 500 (3.4) changed filter | 0.02 | 0.180 | 19.1 | 78.6 | 2.2 |
| 300 (2.1) | 1.1 | 0.139 | 6.3 | 73.7 | 0.1 |
| | 1.2 | 0.133 | 20.2 | 79.8 | 0.0 |
| | 1.5 | 0.126 | 35.1 | 64.9 | 0.0 |
| | 1.5 | 0.116 | 36.1 | 63.9 | 0.0 |
| Batch C: (inverted filter) | | | | | |
| 300 (2.1) | 0.7 | 0.665 | 1.0 | 48.3 | 50.6 |
| | 0.7 | 0.162 | 23.2 | 76.2 | 0.6 |
| | 0.7 | 0.143 | 26.5 | 73.3 | 0.1 |
| | 0.3 | 0.149 | 22.5 | 77.5 | 0.0 |
| 325 (2.2) | 0.5 | 0.144 | 23.6 | 76.3 | 0.0 |

NT—not tested

COMPARATIVE EXAMPLE

For comparison, a sample of the liposomes prepared in Batch C of Example I was extruded through a total of eight passes, first five times through a 90-mm diameter, 200-nm pore size Nuclepore™ polycarbonate filters, two times through a 100-nm Nuclepore™ filter, and once though a 220-nm sterilization filter. (Nuclepore™ filters are commercially available from Nuclepore, Inc., Pleasanton, Calif.) A second sample was extruded in four passes through a 90-mm diameter, 100-nm pore size Anopore™ filter, in accordance with the present invention. As with the first sample, this sample was then passed through a 220-nm sterilization filter. Size data was measured after the pass numbers indicated in the first column. All of the extrusions were conducted at the same pressure of 400 psi (2.8 MPa). The results are presented in Table III:

TABLE III

Mean Diameter and Particle Size Distribution after Extrusion

| Pass Number | Pressure PSI (MPa) | Extrusion Rate Liters/min | Mean Diameter (um) | <0.1 um Percent | 0.1–0.45 um Percent | >0.45 um Percent |
|---|---|---|---|---|---|---|
| | | Sample 1: 200-nm Nuclepore | | | | |
| 5 | 400 (2.8) | 0.7 | 0.195 | 8.5 | 90.1 | 1.4 |
| | | 100-nm Nuclepore | | | | |
| 6 | 400 | 0.3 | 0.168 | 13.5 | 86.3 | 0.3 |
| 7 | 400 | 0.2 | NT | NT | NT | NT |
| | | 220-nm sterile filter | | | | |
| 8 | | NT | 0.152 | 4.0 | 96.1 | 0.0 |
| | | Sample 2: 100-nm Anopore | | | | |
| 2 | 400 (2.8) | 0.7 | 0.174 | 22.0 | 76.9 | 1.1 |
| 4 | 400 | 0.8 | 0.146 | 17.5 | 82.5 | 0.0 |
| | | 220-nm sterile filter | | | | |
| 5 | | NT | 0.150 | 12.0 | 88.0 | 0.0 |

NT—not tested

The branched-pore type aluminum oxide filters of the present invention required fewer passes with a higher flow rate than the polycarbonate filters to obtain a similar particle-size distribution.

EXAMPLE 3

An additional test was conducted to compare the size-reduction capabilities of a branched-pore type anodized aluminum oxide film with an equivalent pore-sized polycarbonate filter. The tests were performed using egg phosphatidylcholine and cholesterol liposomes, made in accordance with Example 1, with the liposomes in aqueous suspension at 100 mg/ml. For this example, the cholesterol was obtained from Croda Chemicals, New York, N.Y. The initial size distribution, as measured on the Malvern Sizer, showed a median diameter of 10.9 um, and a range of diameters of 2.4 to 118 um. To facilitate submicron size reduction, the batch was processed twice through a 5-um Mitex™ PTFE filter at a pressure of 100 psi (0.7 MPa). After this step, the median diameter of the liposomes was measured as 3.5 um, and the range of diameters was 1.9 to 11 um.

The batch was divided into two portions. Portion number one was extruded through a 0.1 micrometer Anopore™ filter, and portion two was extruded through a 0.1 micrometer Nuclepore™ polycarbonate filter. The starting extrusion pressure for both portions was 300 psi (2.1 MPa). The extrusion flow rate, particle size, and particle size distribution were measured for each pass through the filters. A total of five passes were performed on each portion. The results are presented in Table IV:

TABLE IV

Mean Diameter and Particle Size Distribution after Extrusion

| Pass Number | Pressure PSI (MPa) | Extrusion Rate Liters/min | Mean Diameter (um) | <0.1 um Percent | 0.1–0.45 um Percent | >0.45 um Percent |
|---|---|---|---|---|---|---|
| | Portion 1 (Anopore 100-nm filter): | | | | | |
| 1 | 300 (2.1) | 0.6 | 0.565 | 0.0 | 38.6 | 61.4 |
| 2 | 300 | 0.7 | 0.212 | 10.5 | 85.8 | 3.7 |
| 3 | 300 | 0.8 | 0.186 | 10.5 | 88.7 | 0.8 |
| 4 | 300 | 0.8 | 0.172 | 3.6 | 96.4 | 0.0 |
| 5 | 300 | 0.8 | 0.165 | 10.7 | 89.3 | 0.0 |
| | Portion 2 (Nuclenore 100-nm filter): | | | | | |
| 1 | 300 (2.1)–500 (3.4)* | 0.02 | 1.390 | 0.0 | 17.6 | 82.4 |
| 2 | 700 (4.8) | 0.2 | 0.215 | 11.2 | 84.9 | 4.0 |
| 3 | 700 | 0.2 | 0.178 | 6.5 | 93.2 | 0.3 |
| 4 | 700 | 0.2 | 0.167 | 7.4 | 92.6 | 0.0 |
| 5 | 700 | 0.3 | 0.158 | 19.1 | 80.9 | 0.0 |

*—Pressure increased from 300 to 500 psi after 65% filtered.

These data demonstrate that both filters are capable of producing similar size distributions with the same number of passes. However, the aluminum oxide filter used for the first portion required less pressure and operated at a much higher flow rate than the polycarbonate filter used for the second portion. All of the passes through the aluminum oxide filter were conducted at 300 psi (2.1 MPa), with flow rates of 0.6–0.8 liters/min. When the extrusion was repeated using the polycarbonate filter, the initial pressure had to be increased from 300 psi (2.1 MPa) to 500 psi (3.4 MPa) just to complete the first pass through the filter at a very low flow rate of 0.02 liter/min. For passes 2 through 5, a higher pressure of 700 psi (4.8 MPa) was needed to maintain a flow rate of 0.2–0.3 liter/min.

EXAMPLE 4

A further test was conducted to study the differences in the extrusion properties of liposomes with respect to the orientation of the 100 nm Anopore™ branched-pore filter used to size reduce the liposomes. As discussed above, the Anopore 0.1 um branched-pore filter has a small-pore side, having 100 nm pores, and a large-pore side, having 200 nm pores. In this test, a comparison was made to determine the effects of passing aliquots of the same liposome material through the 100 nm Anopore filters with the small-pore side upstream or with the large-pore side upstream.

The test was performed using egg phosphatidylcholine and cholesterol liposomes, made in accordance with Example 1, with the liposomes in aqueous suspension at 100 mg/ml. The material was prepared in a single-five liter lot, mixed well, and divided into four 750 mL samples (A–D). Samples A and B were extruded using the 100-nm upstream orientation, and samples C and D used the 200-nm upstream orientation. Extrusion of the liposomes was carried out by passing them twice though the branched-pore filters, under 400 psig (2.8 MPa) pressure.

The particle size distributions of the filtered materials from each of the test samples were measured using a Nicomp™ sizer, as described in Example 2, and found to be generally equivalent. However, the time required to size reduce the liposomes was significantly less for samples A and B, with the 100-nm filter side upstream, as opposed to samples C and D, with the 200-nm filter side upstream. Table V presents the mean particle size diameter in nanometers (nm) and the filtration time in minutes (min):

TABLE V

Mean Diameters and Extrusion Rates by Filter Orientation

| Sample | Mean Diameter (nm) | | | Filtration Time (min) | |
|---|---|---|---|---|---|
| | Start | Pass 1 | Pass 2 | Pass 1 | Pass 2 |
| A | 199 | 152 | 138 | 0.95 | 0.85 |
| B | 199 | 151 | 131 | 0.52 | 0.53 |
| C | 199 | 157 | 139 | 4.93 | 1.03 |
| D | 199 | 169 | 153 | 3.08 | 0.97 |

The extruded material was then sterile filtered through a 220-nm sterilization filter, of the same type used in the Comparative Example. The sterilization filter used in this test, and in the above Comparative Example, was a commercially available Millipak™ 200 filter supplied by Millipore Corp., Bedford, Mass, and described as having a Durapore™ polyvinylidene difluoride (PVDF) tortuous path membrane. Sterile filtration was considered complete when all of the material had passed through the sterilization filter, or when the steady stream of material had broken into a slow drip. The mean particle diameter (nm), the time required to pass through the filter (min), and the percent volume of material which passed through the sterilization filter were measured for each sample, and the results are presented in Table VI:

TABLE VI

Effect of Extrusion Filter Orientation on Subsequent Sterile Filtration

| Sample | Mean Diameter (nm) | Filtration Time (min) | Percent Through Filter |
|---|---|---|---|
| A | 133 | 2.67 | 96% |
| B | 126 | 0.68 | 100% |
| C | 131 | 1.95 | 47% |
| D | 151 | 1.27 | 44% |

These data demonstrate that the sterile filtration was very efficient for samples A and B, in which almost all of the material successfully passed through the sterilization filter. In contrast, only about half of the volume of samples C and D was able to pass through the sterilization filter before the flow stopped.

EXAMPLE 5

Figure 2:
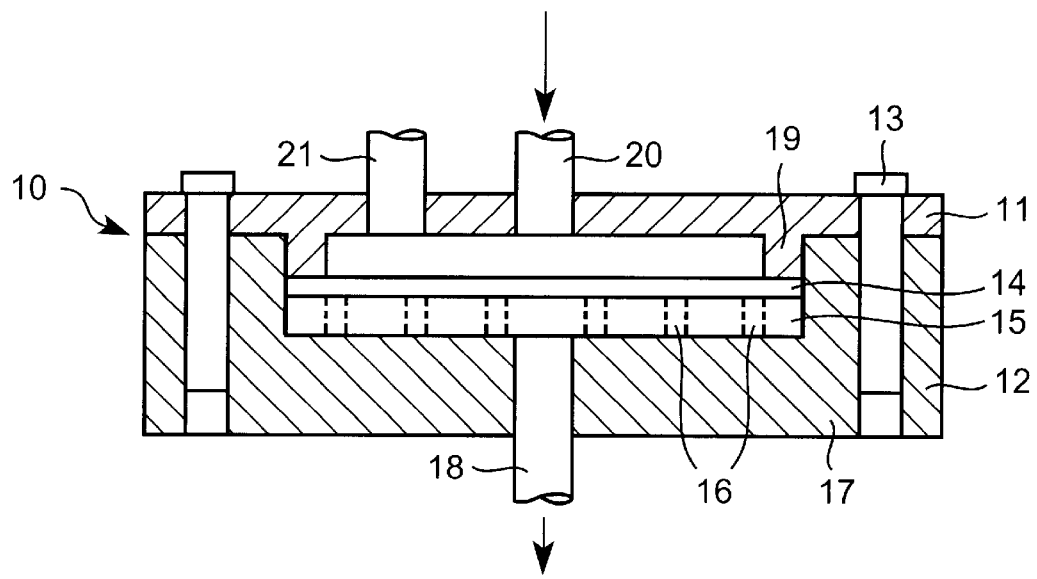
FIG. 2 is a simplified cross-sectional side view, not to scale, through line 2—2 of FIG. 1, of the filter assembly shown in FIG. 1.

FIG. 1 is a simplified top view, not to scale, of a filter assembly (10) made in accordance with a particular embodiment of the present invention, designed for use with a 90-mm diameter Anopore™ filer. It should also be recognized that this filter assembly could also be used to house other types of filters as well, such as, for example, the Nuclepore™ filters used in the comparative tests in Example III above. FIG. 2 is a simplified cross-sectional side view, not to scale, of figure assembly (10) cut along line 2—2 of FIG. 1. Filter assembly (10) comprises a filter housing top half (11) and a filter housing bottom half (12), held together by a plurality of fastening screws (13). Referring to FIG. 2, filter unit (14) represents a 90-mm Anopore filter mounted on a drain disk (Nuclepore Catalog #231700) cut to 90 mm, which is in turn mounted on a 90-mm Teflon$^R$ coated mesh filter support (Millipore Catalog #YY30 090 54). Filter unit (14) is in turn mounted on a stainless steel filter support plate (15), which is provided with fluid passage means, such as transverse channels (16). Support plate (15) sits into a seat portion (17) of filter housing bottom half (12), with the seat portion (17) provided with radial grooves (not shown) to channel the liquid which passes through the filter into liquid outlet (18). Filter housing top half (11) includes a ring portion (19) which holds filter unit (14) in place when top half (11) is tightened down onto bottom half (12) by screws (13).

In operation, the liquid to be filtered enters filter assembly (10) through liquid inlet (20), flows through filter unit (14) and filter support plate (15), and then is channeled out through filter outlet (18). Preferably, housing top half (11) is provided with a relief outlet (21), by which a relief valve (not shown) can be connected to the housing.

Although filter assembly (10) has been described in terms of a "top half" and a "bottom half", these references are for purposes of describing the structure, and do not reflect the orientation of the housing in operation. Because the liquid being filtered is sent to the assembly at such relatively high pressures, it is believed that the assembly can be used in any orientation.

Figure 3:
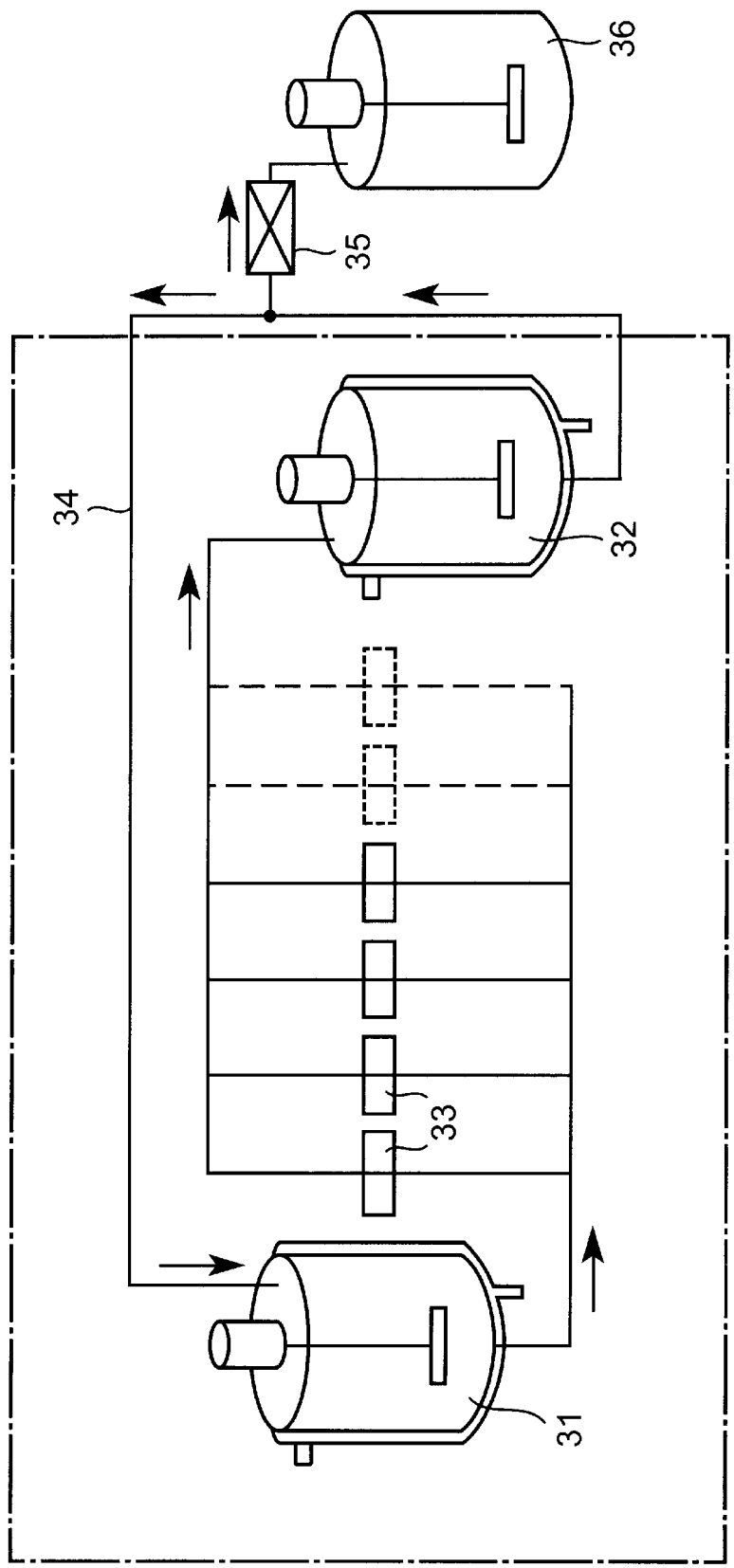
FIG. 3 is a schematic representation of an extrusion system made in accordance with the present invention.

FIG. 3 is a schematic representation of an extrusion system made in accordance with the present invention. The liposome composition to be filtered is contained in a high pressure supply vessel (31), and the filtrate is collected in a similar receiving vessel (32). Both of these vessels are shown as being equipped with stirrers to maintain the liposome mixtures, and heat jacketed for temperature control. The liquid exits supply vessel (31) through a bottom outlet, and is carried through a one or more filter assemblies (33), of the type described above, containing 90-mm Anopore™ filters. The filter assemblies (33) are connected in parallel, with the number of such assemblies used determined by the desired total flow rate from supply vessel (31) to receiving vessel (32). From receiving vessel (32), the filtrate is forced through a sterilization filter (35), such as a Millipak™ 200 filter as described in Example 4 above, and is then collected in a stirred holding vessel (36). In addition, a recycle line (34) may be provided to allow a portion of the output of receiving vessel (32) to be recycled to supply vessel (31).

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

We claim:

1. A method of producing a population of liposomes substantially free of liposomes above a predetermined maximum size, said method comprising:

A. providing a suspension of liposomes, a portion of which are of sizes larger than said predetermined maximum size; and
B. extruding liposomes by passing the suspension of liposomes under a pressure of less than about 600 psi about two to ten times through an aluminum oxide porous film, wherein the film is a nontortuous path, branched-pore type anodic aluminum oxide porous film having a pore size of less than about 200 nm, and wherein the filter comprises:
  (i) an aluminum oxide sheet having two substantially parallel major faces with pores extending from one face of the sheet to the other; and
  (ii) a first system of larger pores extending from one face into the sheet and a second system of smaller pores extending in from the other face, the system of said larger pores interconnecting with the system of said smaller pores such that the inner ends of one or more smaller pores are joined to the inner end of a larger pore and there are substantially no blind pores; and
wherein the liposomes are passed through the aluminum oxide porous film by first entering the film via the smaller pores and extruded via the larger pores.

2. The method of claim 1, wherein the suspension is passed two to ten times.

3. The method of claim 1, wherein the film has a pore size of about 100 nm or less.

4. The method of claim 1, wherein the film has a pore size of about 100 nm.

5. The method of claim 1 further comprising presizing the liposomes before said step of passing the suspension of liposomes through said porous film, said presizing comprising passing the suspension of liposomes one or more times through a filter with a pore size in the range of about 2 to about 10 micrometers.

6. The method of claim 1, wherein the pressure is about 300 psi or less.

7. The method of claim 6, wherein the pressure is about 300 psi.

8. The method of claim 1, wherein the pressure is about 400 psi or less.

9. The method of claim 8, wherein the pressure is about 400 psi.

10. The method of claim 1, wherein the liposomes have a predetermined maximum size of less than about 200 nm, wherein the film has a pore size of about 100 nm, and wherein the pressure is about 300 psi.

11. The method of claim 1, wherein the film has a pore size of about 100 nm, and wherein the pressure is about 400 psi.

12. The method of claim 1, wherein the extrusion is at a flow rate of about 0.6 to about 0.8 liters of the liposome suspension per minute.

\* \* \* \* \*